(12) United States Patent
Ahmed et al.

(10) Patent No.: US 11,878,960 B1
(45) Date of Patent: Jan. 23, 2024

(54) ANTIOXIDANT THERAPEUTIC POTENTIAL OF N,N'-DIPHENYL-1,4-PHENYLENEDIAMINE AND A NOVEL SELENIDE ON MINIMIZING BREAST CANCER HAZARDS

(71) Applicant: KING FAISAL UNIVERSITY, Al-Ahsa (SA)

(72) Inventors: Hany Mohamed Abd El-Lateef Ahmed, Al-Ahsa (SA); Saadeldin Elsayed Ibrahim Shabaan, Al-Ahsa (SA); Mai Mostafa Khalaf Ali, Al-Ahsa (SA); Mohamed Gouda, Al-Ahsa (SA); Shady Gamal El-Sawah, Al-Ahsa (SA); Ibrahim Youssef, Al-Ahsa (SA); Sameh M. Shabana, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/225,424

(22) Filed: Jul. 24, 2023

(51) Int. Cl.
*C07D 239/74* (2006.01)
*A61K 31/517* (2006.01)
*A61K 31/136* (2006.01)

(52) U.S. Cl.
CPC .......... *C07D 239/74* (2013.01); *A61K 31/136* (2013.01); *A61K 31/517* (2013.01)

(58) Field of Classification Search
CPC .............................. A61K 31/517; C07D 239/74
See application file for complete search history.

(56) References Cited

U.S. PATENT DOCUMENTS 6,090,414 A  7/2000 Passwater et al.
2004/0087559 A1  5/2004 Schwartz et al.

OTHER PUBLICATIONS

Shaaban et al. Anti-Cancer Agents in Medicinal Chemistry 2016, 16, 621-632.*
Sak et al. Antioxidants Nov. 2022, 1231, pp. 1-18, published Jun. 23, 2022.*
Carmen Griñan-Lison et al., "Antioxidants for the Treatment of Breast Cancer: Are We There Yet?"; Antioxidants (Basel). Feb. 2021; 10(2): 205., Published online Jan. 31, 2021. https://doi.org/10.3390%2Fantiox10020205.
Emad A. Ahmed, et al., "The antioxidant activity of Vitamin C, DPPD and I-cysteine against Cisplatin-induced testicular oxidative damage in rats"; Food and Chemical Toxicology, vol. 49, Issue 5, May 2011, pp. 1115-1121, https://doi.org/10.1016/j.fct.2011.02.002.

* cited by examiner

*Primary Examiner* — Irina Neagu
(74) *Attorney, Agent, or Firm* — Nath, Goldberg & Meyer; Richard C. Litman

(57) ABSTRACT

Novel organic selenide compounds that can be used as a chemopreventive mixture against breast cancer. These compounds and compositions may be used alone or in conjunction with DPPD. Likewise, the present subject matter relates to the use of N, N'-Diphenyl-1,4-phenylenediamine (DPPD) as a synthetic antioxidant supplementation to enhance breast cancer complications.

6 Claims, No Drawings

ANTIOXIDANT THERAPEUTIC POTENTIAL OF N,N'-DIPHENYL-1,4-PHENYLENEDIAMINE AND A NOVEL SELENIDE ON MINIMIZING BREAST CANCER HAZARDS

BACKGROUND

1. Field

The present disclosure provides novel organic selenide compounds that can be used as a chemopreventive mixture against breast cancer. These compounds and compositions may be used alone or in conjunction with DPPD.

2. Description of the Related Art

According to the World Health Organization (WHO), breast cancer was the most common cancer in 2020 and the second leading cause of death among women worldwide, and its incidence is increasing every day. In recent times, female breast cancer has surpassed lung cancer as the most commonly diagnosed cancer, with an estimated 2.3 million new cases annually. The etiology of breast cancer includes age, late menopause, contraceptive use, hormone therapy, family history, and obesity. These risk factors exert their effects through oxidative stress, evidenced by changes in antioxidant status and altered activities of cellular enzymes, such as SOD, GPX, CAT, TOS, and TAC in the patient's serum.

Breast cancer cells have been shown to be susceptible to oxidative damage and have high levels of oxidative stress, including protein damage, DNA damage, and lipid peroxidation. Further, several breast cancer risk factors may alter levels of endogenous oxidative stress. Oxidative stress mechanisms are involved in the activation of cell signaling pathways, including tumor cell proliferation, increased tumor cell migration, and increased tumor cell proangiogenic factors, and play a key role in apoptosis, mechanisms that can impact both cancer progression and metastasis. Increased ROS and the resulting high oxidative stress are key characteristics of malignant tumors.

Since ROS was linked to almost every step of tumorigenesis, antioxidants have been proposed as potential preventive and therapeutic agents in human cancers. It is the most frequently potent antioxidant used in the oils, rubber, and tire industries. Medically, DPPD is used as an intracellular antioxidant that can affect the efficiency of the microsomal enzymes, increase lipid-soluble antioxidants, inhibit lipid peroxidation and nephrotoxicity, and collagen deposition. DPPD antioxidant activity was attributed to its hydrogen donation capability to radical species, minimizing ROS production and dampening cells' apoptosis.

Large trials were previously conducted to evaluate the preventive effects of antioxidant compounds in a variety of cancers. In 1990, a Chinese trial resulted in the proposition that a mixture of selenium, vitamin E, and (3-carotene supplements significantly reduced cancer mortality from gastric cancer, drawing instant attention to the benefits of the so-called antioxidant therapy. Several types of antioxidants play important roles in ROS homeostasis, including dietary natural antioxidants (vitamins A, C, and E, selenium), endogenous antioxidant molecules (glutathione and melatonin), and endogenous antioxidant enzymes (SOD and CAT). However, few studies rely on synthetic antioxidants in breast cancer therapy.

The development of new synthetic antioxidants having a novel chemical structure for breast cancer therapy as well as pharmaceutical compositions containing the compound as an active ingredient have been desired. Thus, new breast cancer therapies solving the aforementioned problems are desired.

SUMMARY

Thus, the present disclosure provides novel organic selenide compounds that can be used as a chemopreventive mixture against breast cancer. These compounds and compositions may be used alone or in conjunction with DPPD.

Likewise, the present subject matter relates to the use of N, N'-Diphenyl-1,4-phenylenediamine (DPPD) as a synthetic antioxidant supplementation to enhance breast cancer complications.

In an embodiment, the present subject matter relates to a compound having the formula I:

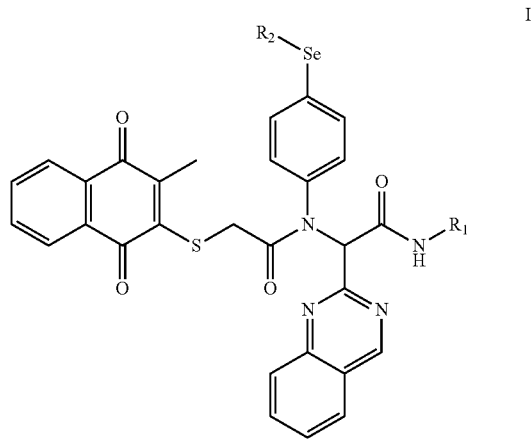

or a pharmaceutically acceptable salt, ester, stereoisomer, or solvate thereof, wherein: $R_1$ is selected from the group consisting of a $C_1$-$C_6$ straight or branched chain alkyl, phenyl, and methylphenyl; and $R_2$ is selected from the group consisting of a $C_1$-$C_6$ straight or branched chain alkyl, phenyl, and methylphenyl.

In another embodiment, the present subject matter relates to a pharmaceutical composition comprising a therapeutically effective amount of a compound as described herein and a pharmaceutically acceptable carrier.

In a further embodiment, the present subject matter relates to a method of inducing an antioxidant response in a patient, comprising administering to a patient in need thereof a therapeutically effective amount of a compound as described herein.

In an embodiment, the present subject matter relates to a method of treating a breast cancer in a patient, comprising administering to a patient in need thereof a therapeutically effective amount of a compound as described herein.

In one embodiment, the present subject matter relates to a method of treating a prostate cancer in a patient, comprising administering to a patient in need thereof a therapeutically effective amount of a compound as described herein.

In another embodiment, the present subject matter relates to a method of treating a breast cancer in a patient, comprising administering to a patient in need thereof a therapeutically effective amount of a compound as described herein and, separately, a therapeutically effective amount of N,N'-Diphenyl-1,4-phenylenediamine (DPPD).

In a further embodiment, the present subject matter relates to a method of treating a prostate cancer in a patient, comprising administering to a patient in need thereof a therapeutically effective amount of a compound as described herein and, separately, a therapeutically effective amount of N,N'-Diphenyl-1,4-phenylenediamine (DPPD).

In an additional embodiment, the present subject matter relates to a compound selected from the group consisting of:

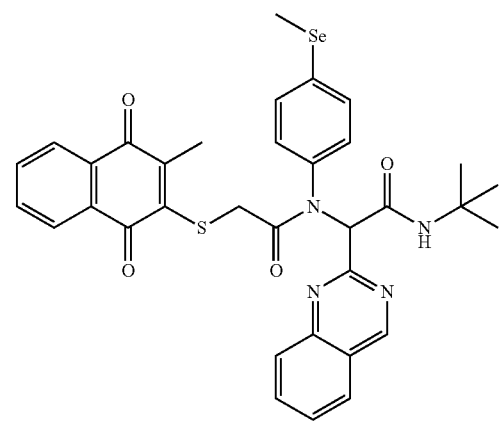

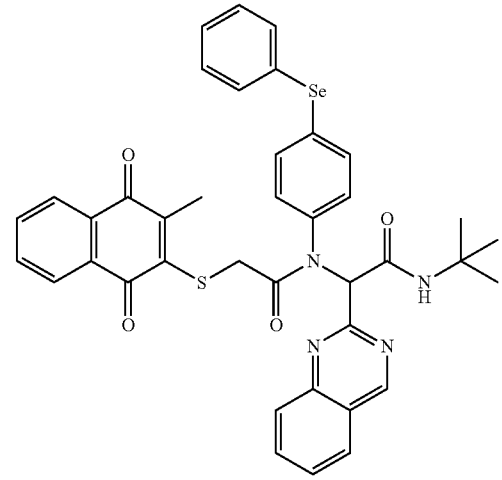

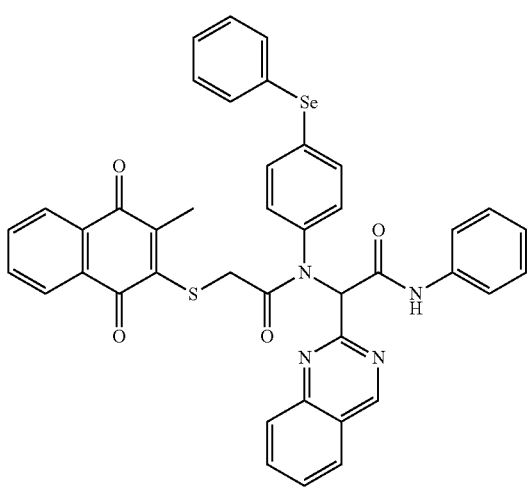

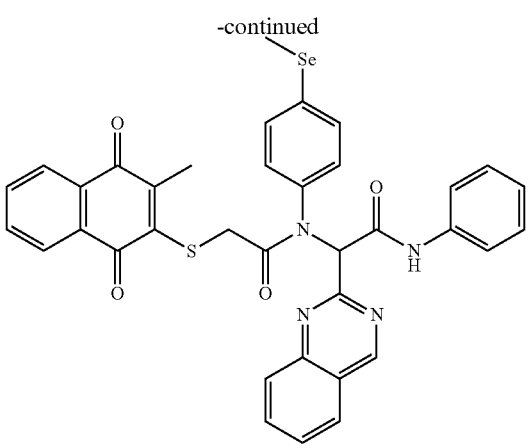

and a pharmaceutically acceptable salt, ester, stereoisomer, or solvate thereof.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., $C_1$-$C_{40}$ alkyl group), for example, 1-30 carbon atoms (i.e., $C_1$-$C_{30}$ alkyl group). In some embodiments, an alkyl group can have 1 to 6 carbon atoms, and can be referred to as a "lower alkyl group" or a "$C_1$-$C_6$ alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

The term "substituted alkyl" as used herein refers to an alkyl group in which 1 or more (up to about 5, for example about 3) hydrogen atoms is replaced by a substituent independently selected from the group: —O, —S, acyl, acyloxy, optionally substituted alkoxy, optionally substituted amino (wherein the amino group may be a cyclic amine), azido, carboxyl, (optionally substituted alkoxy)carbonyl, amido, cyano, optionally substituted cycloalkyl, optionally substituted cycloalkenyl, halogen, hydroxyl, nitro, sulfamoyl, sulfanyl, sulfinyl, sulfonyl, and sulfonic acid. Some of the optional substituents for alkyl are hydroxy, halogen exemplified by chloro and bromo, acyl exemplified by methylcarbonyl; alkoxy, and heterocyclyl exemplified by morpholino and piperidino. Other alkyl substituents as described herein may further be contemplated.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_6$-$C_{24}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzo-dioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —C6F5), are included within the definition of "haloaryl". In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

It will be understood by those skilled in the art with respect to any chemical group containing one or more substituents that such groups are not intended to introduce any substitution or substitution patterns that are sterically impractical and/or physically non-feasible.

The term "isomers" or "stereoisomers" as used herein relates to compounds that have identical molecular formulae but that differ in the arrangement of their atoms in space.

Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as a cancer.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a compound having the formula I:

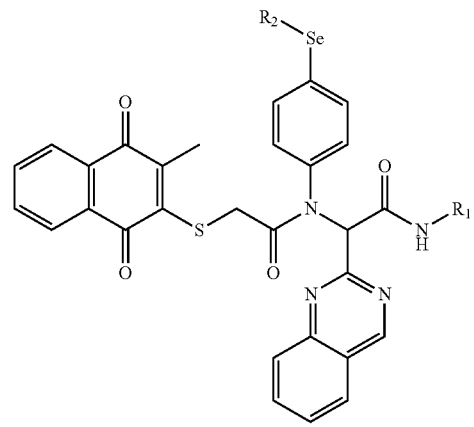

or a pharmaceutically acceptable salt, ester, stereoisomer, or solvate thereof, wherein: $R_1$ is selected from the group consisting of a $C_1$-$C_6$ straight or branched chain alkyl, phenyl, and methylphenyl; and $R_2$ is selected from the group consisting of a $C_1$-$C_6$ straight or branched chain alkyl, phenyl, and methylphenyl.

In certain embodiments, the present subject matter relates to a compound of formula I wherein $R_1$ is selected from the group consisting of —$C(CH_3)_3$, phenyl, and methylphenyl.

In other embodiments, the present subject matter relates to a compound of formula I wherein $R_2$ is selected from the group consisting of methyl, phenyl, and methylphenyl.

In additional embodiments, the present subject matter relates to a compound of formula I wherein $R_1$ is —$C(CH_3)_3$ or phenyl and $R_2$ is methyl or phenyl.

In another embodiment, the present subject matter relates to a compound of formula I wherein the compound is selected from the group consisting of:

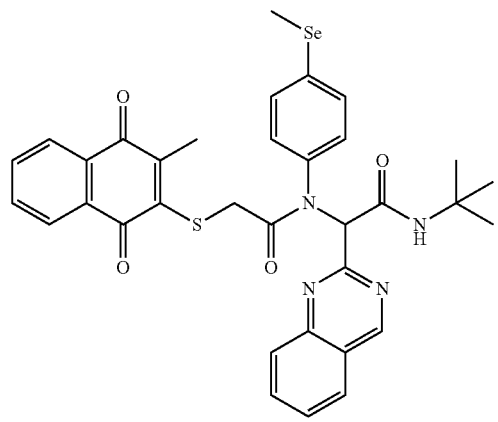

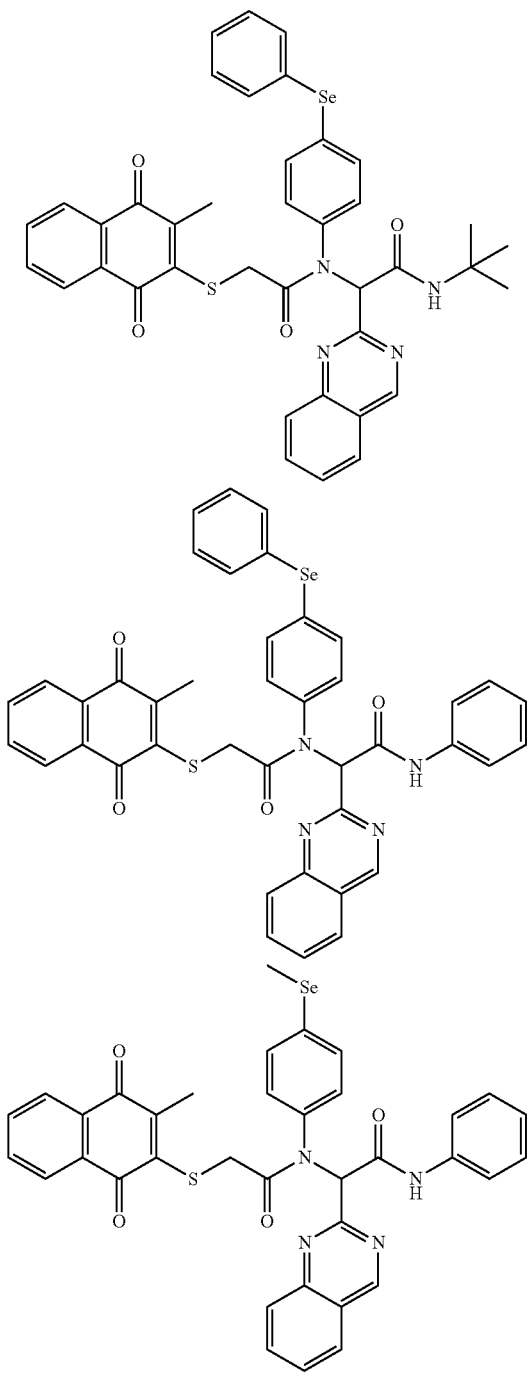

and a pharmaceutically acceptable salt, ester, stereoisomer, or solvate thereof.

It is to be understood that the present subject matter covers all combinations of substituent groups referred to herein.

The present compounds may contain, e.g., when isolated in crystalline form, varying amounts of solvents. Accordingly, the present subject matter includes all solvates of the present compounds of formula I and pharmaceutically acceptable stereoisomers, esters, and/or salts thereof. Hydrates are one example of such solvates.

Further, the present subject matter includes all mixtures of possible stereoisomers of the embodied compounds, independent of the ratio, including the racemates.

Salts of the present compounds, or salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxy-benzoyl)benzoates, butyrates, subsalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers and the salts of the stereoisomers thereof may contain, e.g., when isolated in crystalline form, varying amounts of solvents. Included within the present scope are, therefore, all solvates of the compounds of formula I, as well as the solvates of the salts, the stereoisomers and the salts of the stereoisomers of the compounds of formula I.

The present compounds may be isolated and purified in a manner known per se, e.g., by distilling off the solvent in vacuo and recrystallizing the residue obtained from a suitable solvent or subjecting it to one of the customary purification methods, such as column chromatography on a suitable support material.

Salts of the compounds of formula I and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; a low molecular weight aliphatic ester such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

In one embodiment, the present compounds can be prepared according to the following general synthetic pathway. Specifically, the target organic selenide compound can be synthesized using an Ugi four components reaction. The synthesis starts by the reaction of quinazoline-2-carbaldehyde with 4-($R_2$-selanyl)aniline followed by the addition of 2-((3-methyl-1,4-dioxo-1,4-dihydronaphthalen-2-yl)thio) acetic acid and $R_1$-cyano. The reaction proceeds smoothly at room temperature using methanol as a solvent, as shown in Scheme 1.

Scheme 1

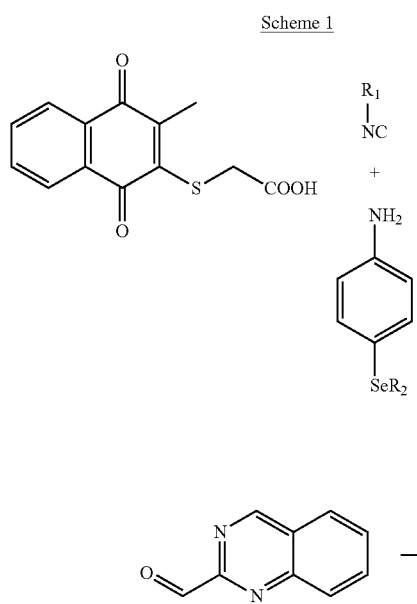

-continued

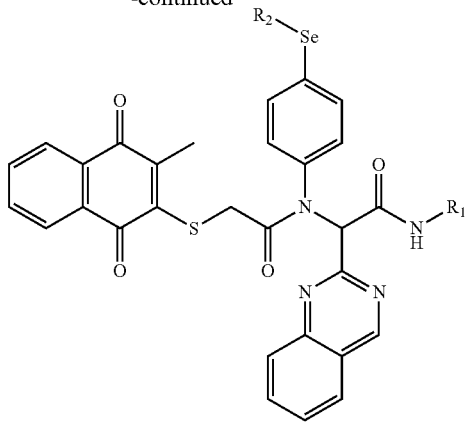

[R1 = C(CH$_3$)$_3$, Ph, CH$_2$Ph; R2= Me, Ph, CH$_2$Ph]

In another embodiment, the present subject matter relates to a pharmaceutical composition comprising a therapeutically effective amount of a compound as described herein and a pharmaceutically acceptable carrier.

In this regard, the present subject matter is directed to pharmaceutical compositions comprising a therapeutically effective amount of the compounds as described herein together with one or more pharmaceutically acceptable carriers, excipients, or vehicles. In some embodiments, the present compositions can be used for combination therapy, where other therapeutic and/or prophylactic ingredients can be included therein, or in combination therapy with another composition containing other components.

Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment for cancer. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg, or even 100 mg/kg, of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for treatment of cancer, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction.

Another manner of administration is parenteral administration, generally characterized by injection, either subcutaneously, intramuscularly, intraperitoneally, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

The present compounds have valuable pharmaceutical properties, which make them commercially utilizable. Accordingly, the present subject matter further relates to use of the present compounds for the treatment of diseases such as cancers. Similarly, the present compounds can be used to inhibit CK2 enzyme activity in a patient.

In a further embodiment, the present subject matter relates to a method of inducing an antioxidant response in a patient, comprising administering to a patient in need thereof a therapeutically effective amount of a compound as described herein.

In an embodiment, the present subject matter relates to a method of treating a breast cancer in a patient, comprising administering to a patient in need thereof a therapeutically effective amount of a compound as described herein.

In one embodiment in this regard, the treating the breast cancer can include providing a chemopreventive effect to the patient who is at risk of developing the breast cancer.

In one embodiment, the present subject matter relates to a method of treating a prostate cancer in a patient, comprising administering to a patient in need thereof a therapeutically effective amount of a compound as described herein.

In another embodiment, the present subject matter relates to a method of treating a breast cancer in a patient, comprising administering to a patient in need thereof a therapeutically effective amount of an organic selenide compound as described herein and, separately, a therapeutically effective amount of N,N'-Diphenyl-1,4-phenylenediamine (DPPD).

In one embodiment in this regard, the organic selenide compound and the DPPD have a synergistic effect in treating the breast cancer.

In another embodiment, the administration of the organic selenide compound and the DPPD significantly decrease the breast cancer's oxidative stress markers.

In a further embodiment, the treating the breast cancer includes providing a chemopreventive effect to the patient who is at risk of developing the breast cancer.

In still another embodiment, the organic selenide compound can be administered to the patent intraperitoneally and the DPPD can be administered to the patent intravenously. In this regard, in an embodiment, about 100 µg/kg of the organic selenide compound and about 250 mg/kg of the DPPD can be administered to the patient.

In a further embodiment, the present subject matter relates to a method of treating a prostate cancer in a patient, comprising administering to a patient in need thereof a therapeutically effective amount of a compound as described herein and, separately, a therapeutically effective amount of N,N'-Diphenyl-1,4-phenylenediamine (DPPD).

In another embodiment of the present subject matter, the organic selenide compounds and/or the DPPD can be used to treat not just breast cancer, but also prostate cancer, lung cancer, colon cancer, melanoma, pancreatic cancer, and/or leukemia.

The present subject matter further relates to a method of treating or preventing a disease comprising administering to a patient in need thereof a therapeutically effective amount of at least one of the compounds herein.

In particular, the present subject matter relates to a method of treating one of the above-mentioned diseases or disorders comprising administering to a patient in need thereof a therapeutically effective amount of at least one of the compounds herein.

In the above methods, the patient is preferably a mammal, more preferably a human. Furthermore, in the above methods, at least one of the present compounds can be used. In an embodiment, one or two of the present compounds are used, or one of the present compounds is used. Similarly, one or more of the present compounds can be used in combination therapy with one or more additional active agents.

The following examples relate to various methods of manufacturing certain specific compounds as described herein. All compound numbers expressed herein are with reference to the synthetic pathway figures shown above.

EXAMPLES

Example 1

The target organoselenium compound 5 is synthesized using the Ugi four components reaction. The synthesis starts by the reaction of quinazoline-2-carbaldehyde (1) (1 mmol) with 4-(methylselanyl)aniline (2) (1 mmol) followed by the addition of 2-((3-methyl-1,4-dioxo-1,4-dihydronaphthalen-2-yl)thio)acetic acid (3) (1 mmol) and 2-isocyano-2-methylpropane (4) (1.2 mmol). The reaction proceeds smoothly at room temperature in methanol as solvent.

Scheme 2

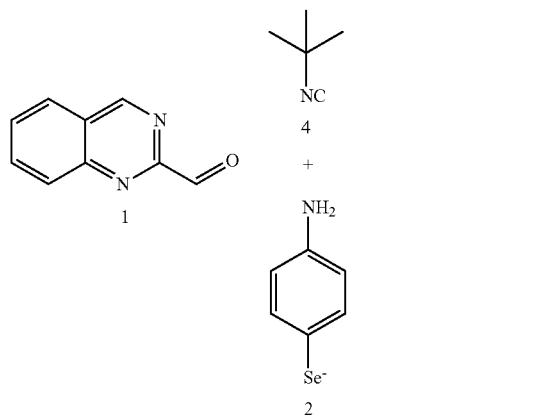

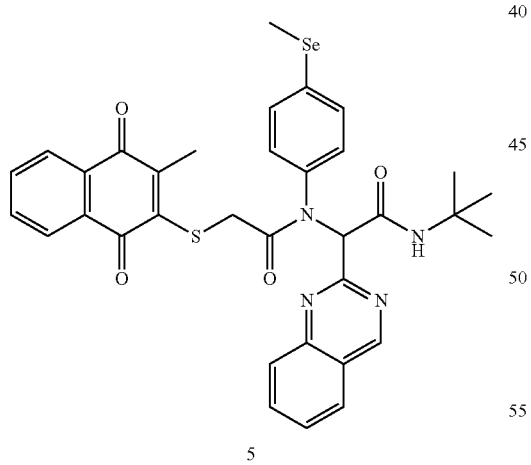

It is to be understood that the organic selenide compounds and the use thereof with DPPD are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A compound of formula I:

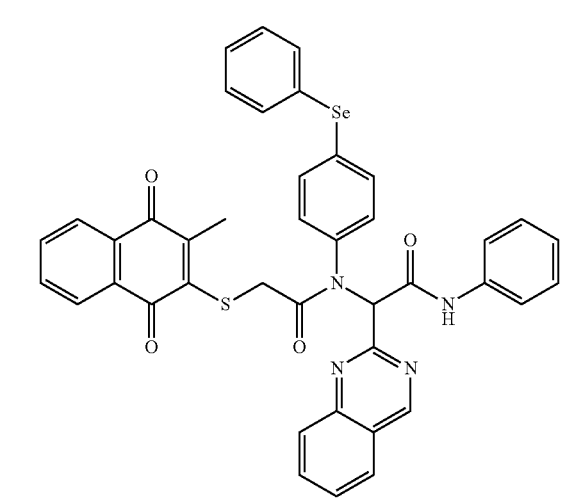

or a pharmaceutically acceptable salt, ester, stereoisomer, or solvate thereof, wherein:

$R_1$ is selected from the group consisting of a $C_1$-$C_6$ straight or branched chain alkyl, phenyl, and methylphenyl; and $R_2$ is selected from the group consisting of a $C_1$-$C_6$ straight or branched chain alkyl, phenyl, and methylphenyl.

2. The compound of claim 1, wherein $R_1$ is selected from the group consisting of —C(CH$_3$)$_3$, phenyl, and methylphenyl.

3. The compound of claim 1, wherein $R_2$ is selected from the group consisting of methyl, phenyl, and methylphenyl.

4. The compound of claim 1, wherein $R_1$ is —C(CH$_3$)$_3$ or phenyl and $R_2$ is methyl or phenyl.

5. A pharmaceutical composition comprising a compound of claim 1 and a pharmaceutically acceptable carrier.

6. A compound selected from the group consisting of:

-continued
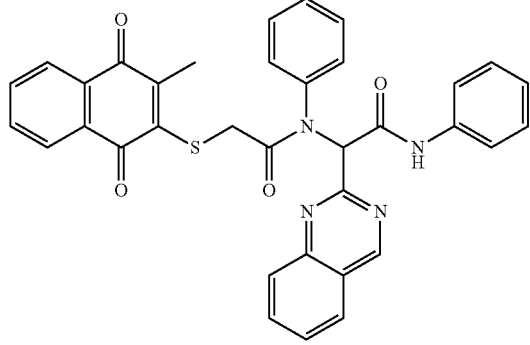
or a pharmaceutically acceptable salt, ester, stereoisomer, or solvate thereof.
* * * * *

UNITED STATES PATENT AND TRADEMARK OFFICE
CERTIFICATE OF CORRECTION

| | |
|---|---|
| PATENT NO. | : 11,878,960 B1 |
| APPLICATION NO. | : 18/225424 |
| DATED | : January 23, 2024 |
| INVENTOR(S) | : Hany Mohamed Abd El-Lateef Ahmed et al. |

It is certified that error appears in the above-identified patent and that said Letters Patent is hereby corrected as shown below:

On the Title Page

Inventors Item (72), for Inventors 5-7, please delete and replace with the updated residences as follows:
SHADY GAMAL EL-SAW AH, Arish, EGYPT; IBRAHIM YOUSSEF, Mansoura, EGYPT; SAMEH M. SHABANA, Mansoura, EGYPT.

Signed and Sealed this
Thirtieth Day of April, 2024

Katherine Kelly Vidal
*Director of the United States Patent and Trademark Office*